(12) United States Patent
Jiang et al.

(10) Patent No.: US 10,308,857 B1
(45) Date of Patent: Jun. 4, 2019

(54) SUPER-AMPHIPHOBIC COMPOSITE MATERIAL AND USE OF THE SAME AS INHIBITOR, LUBRICANT, RESERVOIR PROTECTANT, AND ACCELERATOR IN WATER-BASED DRILLING FLUIDS

(71) Applicant: China University of Petroleum (Beijing), Beijing (CN)

(72) Inventors: Guancheng Jiang, Beijing (CN); Xiaoxiao Ni, Beijing (CN); Lili Yang, Beijing (CN); Guangchang Ma, Beijing (CN); Chunyao Peng, Beijing (CN); Deli Gao, Beijing (CN); Xi Wang, Beijing (CN); Jinsheng Sun, Qingdao (CN); Xiaolin Pu, Chengdu (CN); Kai Wang, Beijing (CN); Zhengqiang Deng, Beijing (CN); Yang Bai, Chengdu (CN); Yinbo He, Beijing (CN); Xinliang Li, Beijing (CN)

(73) Assignee: China University of Petroleum (Beijing) (CN)

( * ) Notice: Subject to any disclaimer, the term of this patent is extended or adjusted under 35 U.S.C. 154(b) by 0 days.

(21) Appl. No.: 16/257,870

(22) Filed: Jan. 25, 2019

(30) Foreign Application Priority Data

Feb. 28, 2018 (CN) .......................... 2018 1 0166488

(51) Int. Cl.
*C09K 8/32* (2006.01)
*C09K 8/03* (2006.01)
*C09K 8/504* (2006.01)
*C09K 8/506* (2006.01)
*C07F 7/08* (2006.01)

(52) U.S. Cl.
CPC .............. *C09K 8/032* (2013.01); *C07F 7/081* (2013.01); *C09K 8/506* (2013.01); *C09K 8/5045* (2013.01); *C09K 2208/10* (2013.01); *C09K 2208/12* (2013.01); *C09K 2208/34* (2013.01)

(58) Field of Classification Search
CPC ....... C07F 7/081; C09K 8/032; C09K 8/5045; C09K 8/506; C09K 2208/10; C09K 2208/12; C09K 2208/34
See application file for complete search history.

(56) References Cited

U.S. PATENT DOCUMENTS

2017/0190961 A1* 7/2017 Nguyen ................ C09K 8/805

FOREIGN PATENT DOCUMENTS

| CN | 101311240 A | 11/2008 |
| CN | 101311242 A | 11/2008 |
| CN | 105802593 A | 7/2016 |

* cited by examiner

*Primary Examiner* — Alicia Bland
(74) *Attorney, Agent, or Firm* — Calfee, Halter & Griswold LLP

(57) ABSTRACT

A super-amphiphobic composite material and use of the same as an inhibitor, lubricant, reservoir protectant, and accelerator in water-based drilling fluids. A method for preparing the amphiphobic composite material includes: performing a first mixing of nano-titanium dioxide and nano-silicon dioxide in an alcohol-water mixed solvent under an alkaline condition, to obtain a dispersion of nano-titanium dioxide and nano-silicon dioxide; then introducing a fluorosilicone-containing coupler into the dispersion of nano-titanium dioxide and nano-silicon dioxide and performing a second mixing. The amphiphobic composite material may be applied in water-based drilling fluids. It has an effect of strongly inhibiting hydrated swelling and disintegration, low toxicity and high compatibility; can solve problems such as well wall instability, blockage of drilling tools, and reservoir damage, etc.; and has long-term practical value in complicated wells such as extra-deep wells, horizontal wells and extended reach wells, and in mud-bearing shale formations.

18 Claims, No Drawings

SUPER-AMPHIPHOBIC COMPOSITE MATERIAL AND USE OF THE SAME AS INHIBITOR, LUBRICANT, RESERVOIR PROTECTANT, AND ACCELERATOR IN WATER-BASED DRILLING FLUIDS

CROSS REFERENCE TO RELATED APPLICATIONS

This application claims priority to Chinese Application No. 201810166488.3, filed on Feb. 28, 2018, entitled "super-amphiphobic composite material and use of the same as inhibitor, lubricant, reservoir protectant, and accelerator in water-based drilling fluids", which is specifically and entirely incorporated by reference.

FIELD OF THE INVENTION

The present invention relates to the oil and gas well drilling field, particularly to a super-amphiphobic composite material and use of the same as inhibitor, lubricant, reservoir protectant, and accelerator in water-based drilling fluids.

BACKGROUND OF THE INVENTION

As drilling techniques are developed increasingly, complicated wells such as extra-deep wells, horizontal wells and extended reach wells, etc. have become the main direction of oil and gas exploration. In the development process of those types of wells, troubles such as blockage during tripping, low penetration rate, jamming of drilling tool, well wall instability, and reservoir damage, etc. may occur easily. Those troubles are largely resulted from the encounter of mud shale formation during drilling. Owing to a fact that mud shale may be hydrated, swell and dispersed easily in conventional drilling fluids, it is difficult to drill to the effective oil and gas reservoir in some areas; in addition, the reservoir may be damaged and severely contaminated due to formation leakage, so as causing adverse effects to subsequent exploitation of the oil and gas reservoir. Therefore, higher and stricter requirements are imposed on the inhibitory additives in drilling fluids. The development of efficient, environment-friendly, and low-cost inhibitors, lubricants, and reservoir protectants has become the top priority in the development of drilling techniques.

At present, all inhibitors, lubricants, and reservoir protectants developed for water-based drilling fluids domestically and abroad have problems such as complex synthesis process, poor high-temperature resistance, and difficulties in large-scale application.

SUMMARY OF THE INVENTION

The objects of the present invention are to provide a super-amphiphobic composite material that can strongly inhibit hydrated swelling and disintegration, has high lubrication performance, high reservoir protection performance, low toxicity, and high compatibility, and use of the super-amphiphobic composite material as inhibitor, lubricant, reservoir protectant, and accelerator in water-based drilling fluids.

To attain the objects described above, in a first aspect, the present invention provides a method for preparing an amphiphobic composite material, comprising:
performing a first mixing of nano-titanium dioxide and nano-silicon dioxide in an alcohol-water mixed solvent under an alkaline condition, to obtain a dispersion of nano-titanium dioxide and nano-silicon dioxide; then introducing a fluorosilicone-containing coupler into the dispersion of nano-titanium dioxide and nano-silicon dioxide and performing a second mixing;
wherein, a molar ratio of the titanium dioxide to the silicon dioxide to the fluorosilicone-containing coupler is 1:0.5-5: 0.01-0.5, particle size of the nano-titanium dioxide is 50-500 nm, and particle size of the nano-silicon dioxide is 50-500 nm.

In a second aspect, the present invention provides an amphiphobic composite material prepared with the above-mentioned method.

In a third aspect, the present invention provides a water-based drilling fluid containing the above-mentioned amphiphobic composite material as inhibitor, lubricant, and reservoir protectant.

In other aspects, the present invention may provide use of the above-mentioned amphiphobic composite material as inhibitor, lubricant, and reservoir protectant in water-based drilling fluids, or use of the above-mentioned water-based drilling fluid in oil and gas well drilling.

The amphiphobic composite material provided in the present invention has hydrophobic and oleophobic properties, and exhibits super-amphiphobicity, especially strong hydrophobicity. It may be used as inhibitor, lubricant, reservoir protectant and accelerator in water-based drilling fluids, and has inhibition, lubrication, reservoir protection, and acceleration performance at the same time, can strongly inhibit hydrated swelling and disintegration, and exhibits a strong lubrication effect for resistance and viscosity reduction and excellent reservoir protection performance. In addition, it has low toxicity and high compatibility, can effectively solve problems such as well wall instability, resistance during tripping, jamming of drilling tool, and reservoir damage, etc., and has long-term practical value and economic benefits for further promoting the development and use of complicated wells such as extra-deep wells, horizontal wells and extended reach wells in mud-containing shale formations.

DETAILED DESCRIPTION OF THE EMBODIMENTS

The ends points and any value in the ranges disclosed in the present invention are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined with each other to obtain one or more new numeric ranges, which shall be deemed as having been disclosed specifically in this document.

In a first aspect, the present invention provides a method for preparing an amphiphobic composite material, comprising:
performing a first mixing of nano-titanium dioxide and nano-silicon dioxide in an alcohol-water mixed solvent under an alkaline condition, to obtain a dispersion of nano-titanium dioxide and nano-silicon dioxide; then introducing a fluorosilicone-containing coupler into the dispersion of nano-titanium dioxide and nano-silicon dioxide and performing a second mixing;
wherein, a molar ratio of the titanium dioxide to the silicon dioxide to the fluorosilicone-containing coupler is 1:0.5-5:

0.01-0.5, particle size of the nano-titanium dioxide is 50-500 nm, and particle size of the nano-silicon dioxide is 50-500 nm.

The amphiphobic composite material prepared with the method of the present invention may be used as amphiphobic inhibitor, lubricant, reservoir protectant and accelerator in water-based drilling fluids. By virtue of "plugging by its physical structure—inhibiting by its chemical properties", the amphiphobic composite material forms an adsorption layer with hydrophobic and oleophobic properties on the surface of mud shale, which not only forms a layer of special nano-micro structures on the surface of mud shale, but also has a plugging effect against tiny pore throats; in addition, with its hydrophobic and oleophobic functional groups on the surface, it can prevent the external water phase from intruding into the spaces among the layers of mud shale, and thereby attains an effect of inhibiting hydrated swelling and disintegration of mud shale. Since the amphiphobic composite material mainly consists of nano-particles in extremely small particle size, a good lubrication effect is achieved among the solid particles. Moreover, owing to its hydrophobic and oleophobic properties, the amphiphobic composite material can modify the wetting property of the surface excellently, prevent the fluid phase from intruding into the reservoir, exhibit high reservoir protection performance, and attain effects of reducing viscosity and filtrate loss in the drilling fluid system, and further promote the application of drilling fluids in mud shale formations.

According to the present invention, by utilizing the effect of the fluorosilicone-containing coupler, the surfaces of nano-titanium dioxide particles and nano-silicon dioxide particles are modified to bear fluorosilicone-containing coupler groups, and usually the nano-titanium dioxide particles and the nano-silicon dioxide particles are bonded among them via the fluorosilicone-containing coupler. Wherein, the molar ratio of the titanium dioxide to the silicon dioxide to the fluorosilicone-containing coupler is 1:0.5-5:0.01-0.5. To ensure that the obtained amphiphobic composite material has better inhibition performance, the molar ratio of the titanium dioxide to the silicon dioxide to the fluorosilicone-containing coupler preferably is 1: 1-3:0.05-0.2, more preferably is 1:1.5-2:0.08-0.15.

According to the present invention, preferably, the particle size of the nano-titanium dioxide is 50-200 nm, and preferably the nano-titanium dioxide particles are nano-titanium dioxide spheres in 50-100 nm particle size.

According to the present invention, preferably, the particle size of the nano-silicon dioxide is 50-200 nm, and preferably the nano-silicon dioxide particles are nano-silicon dioxide spheres in 50-100 nm particle size.

According to the present invention, the fluorosilicone-containing coupler may be selected from a variety of fluorosilicone-containing couplers; preferably, the fluorosilicone-containing coupler is selected from one or more of heptadecafluorodecyl trimethoxysilane, heptadecafluorodecyl triethoxysilane, tridecafluorooctyl trimethoxysilane, tridecafluorooctyl triethoxysilane, dodecafluoroheptyl trimethoxysilane, dodecafluoroheptyl triethoxysilane, nonafluorohexyl trimethoxysilane, nonafluorohexyl triethoxysilane, pentafluorophenyl trimethoxysilane, and pentafluorophenyl triethoxysilane, preferably is one or more of dodecafluoroheptyl trimethoxysilane, dodecafluoroheptyl triethoxysilane, nonafluorohexyl trimethoxysilane, and nonafluorohexyl triethoxysilane.

According to the present invention, to promote the bonding between the nano-titanium dioxide and nano-silicon dioxide and the fluorosilicone-containing coupler, an alcohol-water mixed solvent is used in the present invention, the alcohol solvent in the alcohol-water mixed solvent may be selected from a variety of alcohol solvents, and preferably is one or more of ethanol, methanol, n-propanol, and iso-propanol. Wherein, in the alcohol-water mixed solvent, the volume ratio of alcohol solvent to water preferably is 1:2-10.

According to the present invention, the dose of the alcohol-water mixed solvent may vary in a wide range; preferably, with respect to 100 g total weight of the nano-titanium dioxide and the nano-silicon dioxide, the dose of the alcohol-water mixed solvent is 500-1,500 mL.

According to the present invention, the pH of the alkaline condition preferably is 8-10, more preferably is 8-9. Such an alkaline condition may be achieved by adjusting with a conventional pH adjusting alkaline substance in the art. For example, one or more of alkali hydroxides (e.g., sodium hydroxide, potassium hydroxide, and lithium hydroxide, etc.) and their water solutions, alkali carbonates (e.g., sodium carbonate and potassium carbonate, etc.) and their water solutions, and ammonia water may be used.

According to the present invention, the purpose of the first mixing is to fully disperse the nano-titanium dioxide and the nano-silicon dioxide in the alcohol-water mixed solvent. To that end, preferably, the first mixing is performed by ultrasonic dispersion. Wherein, the conditions of the first mixing preferably include: a temperature of 10-40° C., an ultrasonic dispersion time of 10-30 min.

According to the present invention, the fluorosilicone-containing coupler is introduced in the process of the second mixing. The fluorosilicone-containing coupler is described above. To achieve better bonding between the fluorosilicone-containing coupler and the nano-titanium dioxide and nano-silicon dioxide, preferably the conditions of the second mixing include: a temperature of 55-95° C., a stirring rate of 200-500 rpm, a time of 8-20 h; more preferably, the conditions of the second mixing include: a temperature of 60-80° C., a stirring rate of 350-500 rpm, a time of 10-15 h.

According to the present invention, to extract the amphiphobic composite material, the method may further comprise: performing solid-liquid separation of the product of the second mixing (e.g., by centrifugal separation), washing the solid phase (e.g., by water washing), and drying the solid phase (e.g., drying for 0.5-10 h at 50-120° C.), so as to obtain the amphiphobic composite material.

In a second aspect, the present invention provides an amphiphobic composite material prepared with the above-mentioned method.

In the amphiphobic composite material prepared in the present invention, both the surfaces of the nano-titanium dioxide and the nano-silicon dioxide are modified to bear the fluorosilicone-containing coupler; furthermore, bonds are formed via the fluorosilicone-containing coupler among the nano-titanium dioxide particles, among the nano-silicon dioxide particles, and between the nano-titanium dioxide particles and the nano-silicon dioxide particles. Thus, the fluorosilicone-containing coupler exhibits excellent inhibition performance and can effectively inhibit hydrated disintegration of bentonite core pieces, reduce friction resistance, and protect the oil and gas reservoir.

According to the present invention, the above-mentioned amphiphobic composite material can be used as inhibitor, lubricant, reservoir protectant, and accelerator in water-based drilling fluids.

That is to say, when the amphiphobic composite material provided in the present invention is used as an additive in a water-based drilling fluid, it attains inhibition effect, lubrication effect, reservoir protection effect and penetration rate accelerating effect, and thereby achieves multi-purpose effects. Therefore, it may also be expressed as the present invention provide a use of the above-mentioned amphiphobic composite material as an additive that has inhibition effect, lubrication effect, reservoir protection effect, and acceleration effect in water-based drilling fluids.

In a third aspect, the present invention provides a water-based drilling fluid containing the above-mentioned amphiphobic composite material as inhibitor, lubricant, and reservoir protectant. The subject matter may also be expressed as a water-based drilling fluid that contains the above-mentioned amphiphobic composite material as an additive that has inhibition effect, lubrication effect, reservoir protection effect, and acceleration effect.

According to the present invention, as described above, a water-based drilling fluid that employs the above-mentioned amphiphobic composite material as inhibitor, lubricant, reservoir protectant and accelerator obtains excellent inhibition performance, lubrication performance, reservoir protection performance and penetration rate accelerating performance. The content of the amphiphobic composite material may vary within a wide range. Preferably, based on the total weight of the water-based drilling fluid excluding weighting agent, the content of the amphiphobic composite material is 0.1-0.5 wt %, more preferably is 0.2-0.5 wt %.

In addition, as a water-based drilling fluid, the drilling fluid provided in the present invention may further contains conventional additives for water-based drilling fluids in the art. For example, based on the total weight of the water-based drilling fluid excluding a weighting agent, the drilling fluid may contain 3-6 wt % bentonite (e.g., sodium bentonite and/or calcium bentonite), 0.1-1 wt % temperature-resistant filtrate reducer (e.g., one or more of modified sodium humate polycondensate (KJAN), phenolic resin, sulfomethylated phenolic resin, and sulfomethylated lignite resin, etc.), 0.5-2 wt % salinity-resistant filtrate reducer (e.g., one or more of cellulose ether derivatives (PAC), starch, modified starch, and carboxymethyl cellulose, etc.), 0.5-2 wt % plugging agent (e.g., one or more of superfine calcium carbonate powder, albino asphalt, and commercial plugging agent ZHFD-1, etc.), and weighting agent (e.g., one or more of barite (e.g., barite with 90 wt % or higher content of barium sulfate), and organic salts (weigh-1, weigh-2 (the active component is potassium formate), weigh-3, organic sodium salt GD-WT), etc.), so that the water-based drilling fluid obtains required density, e.g., 1-3 g/cm$^3$.

According to the present invention, the above-mentioned water-based drilling fluid can be used in oil and gas well drilling.

Since the water-based drilling fluid obtained in the present invention contains the amphiphobic composite material in the present invention as inhibitor, lubricant, reservoir protectant, and accelerator, the water-based drilling fluid obtains excellent inhibition performance, lubrication performance, reservoir protection performance and well-drilling penetration rate accelerating performance, and has high compatibility, and the amphiphobic composite material essentially has no adverse effect to the rheological property of the water-based drilling fluid. Therefore, the water-based drilling fluid is applicable to mining in complicated wells, such as extra-deep wells, horizontal wells, and extended reach wells, etc.

Hereunder the present invention will be detailed in embodiments.

Example 1

This example is provided to describe the amphiphobic composite material and its preparation method in the present invention.

Nano-titanium dioxide particles (nano-titanium dioxide spheres in 100 nm particle size) and nano-silicon dioxide particles (nano-silicon dioxide spheres in 100 nm particle size) in 5 g total weight (wherein, the molar ratio of the titanium dioxide to the silicon dioxide is 1:1) are added into 50 mL mixed solvent of ethanol and water (the volume ratio of ethanol to water is 1:2), the pH of the system is adjusted to 8 with ammonia water, then the system is treated by ultrasonic dispersion at 25° C. for 20 min, to obtain a dispersion; next, dodecafluoroheptyl trimethoxysilane is added into the dispersion (the dodecafluoroheptyl trimethoxysilane is dosed so that the molar ratio of the titanium dioxide to the dodecafluoroheptyl trimethoxysilane is 1:0.1), the resultant mixture is stirred at 60° C. at 500 rpm stirring rate for 12 h for reaction; the obtained product is centrifuged, the obtained solid phase is washed with water and then dried at 80° C.; thus, an amphiphobic composite material is obtained and denoted as AN-1.

Example 2

This example is provided to describe the amphiphobic composite material and its preparation method in the present invention.

Nano-titanium dioxide particles (nano-titanium dioxide spheres in 100 nm particle size) and nano-silicon dioxide particles (nano-silicon dioxide spheres in 100 nm particle size) in 5 g total weight (wherein, the molar ratio of the titanium dioxide to the silicon dioxide is 1:1.5) are added into 50 mL mixed solvent of methanol and water (the volume ratio of methanol to water is 1:5), the pH of the system is adjusted to 8.5 with ammonia water, then the system is treated by ultrasonic dispersion at 25° C. for 15 min, to obtain a dispersion; next, dodecafluoroheptyl trimethoxysilane is added into the dispersion (the dodecafluoroheptyl trimethoxysilane is dosed so that the molar ratio of the titanium dioxide to the dodecafluoroheptyl trimethoxysilane is 1:0.15), the resultant mixture is stirred at 65° C. at 450 rpm stirring rate for 12 h for reaction; the obtained product is centrifuged, the obtained solid phase is washed with water and then dried at 80° C.; thus, an amphiphobic composite material is obtained and denoted as AN-2.

Example 3

This example is provided to describe the amphiphobic composite material and its preparation method in the present invention.

Nano-titanium dioxide particles (nano-titanium dioxide spheres in 100 nm particle size) and nano-silicon dioxide particles (nano-silicon dioxide spheres in 100 nm particle size) in 5 g total weight (wherein, the molar ratio of the titanium dioxide to the silicon dioxide is 1:2) are added into 50 mL mixed solvent of ethanol and water (the volume ratio of ethanol to water is 1:2), the pH of the system is adjusted to 9 with ammonia water, then the system is treated by ultrasonic dispersion at 25° C. for 20 min, to obtain a dispersion; next, dodecafluoroheptyl trimethoxysilane is added into the dispersion (the dodecafluoroheptyl trimethoxysilane is dosed so that the molar ratio of the titanium dioxide to the dodecafluoroheptyl trimethoxysilane is 1:0.2), the resultant mixture is stirred at 75° C. at 500 rpm stirring rate for 10 h for reaction; the obtained product is centrifuged, the obtained solid phase is washed with water and then dried at 80° C.; thus, an amphiphobic composite material is obtained and denoted as AN-3.

Example 4

This example is provided to describe the amphiphobic composite material and its preparation method in the present invention.

The method described in the example 1 is used, but the difference is that the molar ratio of the titanium dioxide to the silicon dioxide is 1:0.5, though the total weight of the nano-titanium dioxide particles and the nano-silicon dioxide particles remains unchanged; finally, an amphiphobic composite material is obtained and denoted as AN-4.

Example 5

This example is provided to describe the amphiphobic composite material and its preparation method in the present invention.

The method described in the example 1 is used, but the difference is that the molar ratio of the titanium dioxide to the silicon dioxide is 1:4.5, though the total weight of the nano-titanium dioxide particles and the nano-silicon dioxide particles remains unchanged; finally, an amphiphobic composite material is obtained and denoted as AN-5.

Example 6

This example is provided to describe the amphiphobic composite material and its preparation method in the present invention.

The method described in the example 1 is used, but the difference is that the dodecafluoroheptyl trimethoxysilane is dosed so that the molar ratio of the titanium dioxide to the dodecafluoroheptyl trimethoxysilane is 1:0.04; finally, an amphiphobic composite material is obtained and denoted as AN-6.

Example 7

This example is provided to describe the amphiphobic composite material and its preparation method in the present invention.

The method described in the example 1 is used, but the difference is that the dodecafluoroheptyl trimethoxysilane is dosed so that the molar ratio of the titanium dioxide to the dodecafluoroheptyl trimethoxysilane is 1:0.5; finally, an amphiphobic composite material is obtained and denoted as AN-7.

Examples 8-11

This example is provided to describe the amphiphobic composite material and its preparation method in the present invention.

The method described in the example 1 is used, but the difference is as following:

In example 8, the dodecafluoroheptyl trimethoxysilane is replaced with heptadecafluorodecyl trimethoxysilane in the same molar amount; finally an amphiphobic composite material is obtained and denoted as AN-8;

In example 9, the dodecafluoroheptyl trimethoxysilane is replaced with tridecafluorooctyl trimethoxysilane in the same molar amount; finally an amphiphobic composite material is obtained and denoted as AN-9;

In example 10, the dodecafluoroheptyl trimethoxysilane is replaced with nonafluorohexyl trimethoxysilane in the same molar amount; finally an amphiphobic composite material is obtained and denoted as AN-10;

In example 11, the dodecafluoroheptyl trimethoxysilane is replaced with pentafluorophenyl trimethoxysilane in the same molar amount; finally an amphiphobic composite material is obtained and denoted as AN-11.

Reference Example 1

The method described in the example 1 is used, but the difference is that the nano-silicon dioxide particles are omitted, and only the nano-titanium dioxide particles are used and the total weight of the nano-titanium dioxide particles is 5 g; finally, an amphiphobic composite material is obtained and denoted as DAN-1.

Reference Example 2

The method described in the example 1 is used, but the difference is that the nano-titanium dioxide particles are omitted, and only the nano-silicon dioxide particles are used and the total weight of the nano-silicon dioxide particles is 5 g; finally, an amphiphobic composite material is obtained and denoted as DAN-2.

Reference Example 3

The method described in the example 1 is used, but the difference is that the molar ratio of the titanium dioxide to the silicon dioxide is 1:0.1, though the total weight of the nano-titanium dioxide particles and the nano-silicon dioxide particles remains unchanged; finally, an amphiphobic composite material is obtained and denoted as DAN-3.

Reference Example 4

The method described in the example 1 is used, but the difference is that the molar ratio of the titanium dioxide to the silicon dioxide is 1:8, though the total weight of the nano-titanium dioxide particles and the nano-silicon dioxide particles remains unchanged; finally, an amphiphobic composite material is obtained and denoted as DAN-4.

Reference Example 5

The method described in the example 1 is used, but the difference is that the nano-titanium dioxide particles are nano-titanium dioxide spheres in 20 nm particle size, and the nano-silicon dioxide particles are nano-silicon dioxide spheres in 20 nm particle size; finally, an amphiphobic composite material is obtained and denoted as DAN-5.

Reference Example 6

The method described in the example 1 is used, but the difference is that the nano-titanium dioxide particles are nano-titanium dioxide spheres in 800 nm particle size, and the nano-silicon dioxide particles are nano-silicon dioxide spheres in 800 nm particle size; finally, an amphiphobic composite material is obtained and denoted as DAN-6.

Test Case 1

Measurement of hydrophobic and oleophobic properties of rock surface: 0.3 wt % water solutions of the above-mentioned amphiphobic composite materials are prepared respectively as solutions to be tested, and the amphiphobic composite material AN-1 is prepared into 3 solutions to be test with different concentrations respectively (0.1 wt %, 0.3 wt %, and 0.5 wt %); artificial rock cores are placed in the solutions and soaked for 8 h at 160° C.; then the rock cores are taken out, and cooled and dried naturally, and then the contact angles $\theta_o$ and $\theta_w$ of oil phase and water phase on the surfaces of the rock cores are measured with a contact angle meter (JC2000D3 contact angle meter from Shanghai Zhongchen Digital Technology and Equipment Co., Ltd.). The results are shown in Table 1, wherein, the oil phase test liquid is n-cetane, and the water phase test liquid is distilled water.

TABLE 1

| Amphiphobic composite material/concentration (wt %) | $\theta_w/(°)$ | $\theta_o/(°)$ |
|---|---|---|
| AN-1/0.1 | 61.4 | 49.8 |
| AN-1/0.3 | 122.5 | 103.4 |
| AN-1/0.5 | 122.9 | 104.6 |
| AN-2/0.3 | 118.7 | 99.6 |
| AN-3/0.3 | 123.4 | 105.1 |
| AN-4/0.3 | 115.8 | 94.7 |
| AN-5/0.3 | 111.3 | 90.6 |
| AN-6/0.3 | 112.5 | 90.5 |
| AN-7/0.3 | 118.4 | 96.6 |
| AN-8/0.3 | 120.3 | 100.1 |
| AN-9/0.3 | 118.5 | 100.3 |
| AN-10/0.3 | 114.7 | 97.2 |
| AN-11/0.3 | 112.5 | 93.9 |
| DAN-1/0.3 | 91.2 | 77.6 |
| DAN-2/0.3 | 93.6 | 75.8 |
| DAN-3/0.3 | 93.5 | 77.9 |
| DAN-4/0.3 | 94.2 | 74.1 |
| DAN-5/0.3 | 92.4 | 73.8 |
| DAN-6/0.3 | 91.8 | 74.5 |

It is seen from the data in Table 1: the amphiphobic composite material provided in the present invention can modify the rock surface to be hydrophobic and oleophobic.

Test Case 2

The above-mentioned amphiphobic composite material AN-1 is dispersed in water to obtain aqueous dispersions at 0.1 wt %, 0.3 wt %, and 0.5 wt % concentrations respectively; the amphiphobic composite materials AN-1 to AN-11 and DAN-1 to DAN-8 are dispersed in water to obtain aqueous dispersions at 0.3 wt % concentration respectively; and 7 wt % water solution of potassium chloride, 2 wt % water solution of polyetheramine (designation sigma-adrich from Energy Chemical, the same below), and clean water are prepared; the swelling height of artificial well cores is measured with a shale swelling tester at 2 h, 12 h and 24 h as per the industry standard SY/T6335-1997 Evaluation Procedure of Drilling Fluids Shale Inhibitor, to evaluate the inhibition performance of the above-mentioned aqueous dispersions, water solution of potassium chloride, polyetheramine solution, and clean water; the results are shown in Table 2.

TABLE 2

| | Swelling height at 2 h mm | Swelling height at 12 h mm | Swelling height at 24 h mm |
|---|---|---|---|
| 0.1 wt % AN-1 | 1.18 | 2.21 | 3.08 |
| 0.3 wt % AN-1 | 0.72 | 1.34 | 2.15 |
| 0.5 wt % AN-1 | 0.74 | 1.29 | 2.19 |
| 0.3 wt % AN-2 | 0.75 | 1.31 | 2.20 |
| 0.3 wt % AN-3 | 0.81 | 1.34 | 2.17 |
| 0.3 wt % AN-4 | 0.86 | 1.40 | 2.28 |
| 0.3 wt % AN-5 | 0.88 | 1.43 | 2.33 |
| 0.3 wt % AN-6 | 0.94 | 1.49 | 2.39 |
| 0.3 wt % AN-7 | 0.82 | 1.36 | 2.45 |
| 0.3 wt % AN-8 | 0.78 | 1.33 | 2.37 |
| 0.3 wt % AN-9 | 0.81 | 1.38 | 2.41 |
| 0.3 wt % AN-10 | 0.85 | 1.42 | 2.44 |
| 0.3 wt % AN-11 | 0.88 | 1.46 | 2.47 |
| 0.3 wt % DAN-1 | 0.94 | 1.50 | 2.51 |
| 0.3 wt % DAN-2 | 0.93 | 1.49 | 2.56 |
| 0.3 wt % DAN-3 | 0.97 | 1.58 | 2.64 |
| 0.3 wt % DAN-4 | 0.98 | 1.61 | 2.69 |
| 0.3 wt % DAN-5 | 0.97 | 1.65 | 2.72 |
| 0.3 wt % DAN-6 | 1.02 | 1.62 | 2.71 |
| 7 wt % KCl | 1.36 | 3.47 | 3.61 |
| 2 wt % polyetheramine | 1.01 | 2.90 | 3.64 |
| Clean water | 2.01 | 4.65 | 5.99 |

It is seen from Table 2: the amphiphobic inhibitor in the present invention exhibits a good inhibition effect, the swelling height of the bentonite is increased continuously as the time elapses, but essentially doesn't vary anymore after 24 h; besides, as the concentration of the amphiphobic inhibitor is increased, the swelling height of the bentonite is decreased continuously, the swelling height of the bentonite is the smallest when the concentration of the amphiphobic inhibitor is 0.3%, and doesn't vary obviously when the concentration of the amphiphobic inhibitor is further increased; compared with the conventional 7 wt % KCl solution and 2% polyetheramine solution, the clay swelling inhibition performance of the amphiphobic inhibitor provided in the present invention is better, and the clay swelling amount in the amphiphobic inhibitor is much smaller than the clay swelling amount in the clean water solution within 24 h.

Test Case 3

The hot rolling recovery ratio is measured as per the industry standard SY/T5613-2000 Methods for Testing Physical and Chemical Properties of Mud Shale, mainly through the following steps: 350 mL test solutions (0.3 wt % dispersion of the above-mentioned amphiphobic composite material dispersed in water, 2 wt % water solution of potassium chloride, and 2 wt % polyetheramine solution respectively) are loaded into an aging can respectively, 50 g 5-10 mesh mud shale cuttings are weighed and added into the test solutions, and then are dispersed in a roller furnace at 120° C. for 16 h, respectively; then, the recovered rock sample is screened through a 40 mesh screen in water to clean state, and the residual rock sample is loaded into a watch glass, and then is dried in an oven at 105° C. to constant weight; the weight is measured, and the hot-aging recovery rate is calculated with the following formula (the result is shown in Table 3):

$$S = M/50 \times 100\%$$

Where, S—recovery ratio after screening through a 40 mesh screen, %; M—screen residue after screening though the 40 mesh screen, g.

TABLE 3

| | Rolling Recovery Ratio/% |
|---|---|
| 0.3 wt % AN-1 | 72.1 |
| 0.3 wt % AN-2 | 71.8 |
| 0.3 wt % AN-3 | 72.1 |
| 0.3 wt % AN-4 | 68.9 |
| 0.3 wt % AN-5 | 67.8 |
| 0.3 wt % AN-6 | 65.5 |
| 0.3 wt % AN-7 | 63.8 |

TABLE 3-continued

|  | Rolling Recovery Ratio/% |
|---|---|
| 0.3 wt % AN-8 | 70.4 |
| 0.3 wt % AN-9 | 70.8 |
| 0.3 wt % AN-10 | 65.9 |
| 0.3 wt % AN-11 | 66.1 |
| 0.3 wt % DAN-1 | 58.9 |
| 0.3 wt % DAN-2 | 57.6 |
| 0.3 wt % DAN-3 | 59.5 |
| 0.3 wt % DAN-4 | 59.1 |
| 0.3 wt % DAN-5 | 50.4 |
| 0.3 wt % DAN-6 | 52.0 |
| 2 wt % KCl | 38.9 |
| 2 wt % polyetheramine | 51.6 |
| Clean water | 11.2 |

It is seen from the results in Table 3: the amphiphobic composite material provided in the present invention can effective inhibit hydration of shale particles and attain a purpose of improving the rolling recovery ratio of shale, and is an excellent amphiphobic inhibitor. Compared with clean water, the amphiphobic composite material provided in the present invention can greatly improve the rolling recovery ratio of shale; besides, compared with 2 wt % KCl and 2 wt % polyetheramine solution, the amphiphobic composite material can also improve the rolling recovery ratio excellently.

Test Case 4

Preparation of base mud: 40 g sodium bentonite (from Weifang Huawei Bentonite Technology Research Center, the same below) and 3 g anhydrous sodium carbonate are added into 1 L water, the mixture is stirred at a high stirring rate for 5 h, and kept in still state in a sealed state at room temperature for 24 for curing, to obtain fresh water base mud that has 4 wt % soil content.

The lubrication coefficients of the above-mentioned base mud and base muds admixed with the amphiphobic composite material AN-1 in specified contents (the contents are shown in Table 4) are measured respectively; next, the base muds are aged at 150° C. for 16 h, and then the lubrication coefficients are measured again, and the reduction ratios of the lubrication coefficients are obtained through calculation; the results are shown in Table 4.

Where, lubrication coefficient test: the extreme pressure lubrication coefficients of the tested liquid are measured with a Fann EP extreme pressure lubrication tester before and after the liquid is aged at 150° C. for 16 h, and the reduction ratio of lubrication coefficient is calculated.

Wherein, reduction ratio of lubrication coefficient=(extreme pressure lubrication coefficient of the base mud−extreme pressure lubrication coefficient of the base mud that contains the amphiphobic composite material AN-1)/extreme pressure lubrication coefficient of the base mud× 100%.

TABLE 4

|  | EP Lubrication coefficient | Reduction ratio of lubrication coefficient |
|---|---|---|
|  | Before aging | |
| Base mud | 0.54 | / |
| Base mud + 0.1 wt % AN-1 | 0.22 | 59.3% |
| Base mud + 0.2 wt % AN-1 | 0.17 | 68.5% |
| Base mud + 0.3 wt % AN-1 | 0.11 | 80.0% |
| Base mud + 0.4 wt % AN-1 | 0.11 | 80.0% |
| Base mud + 0.5 wt % AN-1 | 0.11 | 80.0% |

TABLE 4-continued

|  | EP Lubrication coefficient | Reduction ratio of lubrication coefficient |
|---|---|---|
|  | After aging for 16 h at 150° C. | |
| Base mud | 0.52 | / |
| Base mud + 0.1 wt % AN-1 | 0.19 | 63.5% |
| Base mud + 0.2 wt % AN-1 | 0.14 | 73.1% |
| Base mud + 0.3 wt % AN-1 | 0.09 | 82.7% |
| Base mud + 0.4 wt % AN-1 | 0.09 | 82.7% |
| Base mud + 0.5 wt % AN-1 | 0.09 | 82.7% |

It is seen from the results in Table 4: the amphiphobic composite material provided in the present invention can effectively decrease the extreme pressure lubrication coefficient of the base mud of drilling fluid and attain the purpose of reducing friction resistance, and is an excellent amphiphobic lubricant. The lubrication coefficient can be decreased by 80.0% at normal temperature, and can be decreased by 82.7% after the amphiphobic composite material is aged at 120° C. That indicates the amphiphobic composite material provided in the present invention has excellent lubrication performance.

Test Case 5

Composition of water-based drilling fluid $1^\#$: 3 wt % sodium bentonite (from Weifang Huawei Bentonite Technology Research Center, the same below), 0.5 wt % sulfomethylated phenolic resin filtrate reducer (SMP-II from Xinxiang Xinlei Oil Field Additives Co., Ltd., the same below), 1 wt % albino asphalt plugging agent (from Henan Haiyang Chemical Co., Ltd.), and 1 wt % starch; in addition, water and barite are added to adjust the density of the drilling fluid to 1.2 g/cm³.

Composition of water-based drilling fluid $2^\#$: the composition of the water-based drilling fluid 1# is used, but the difference is that the amphiphobic composite material AN-1 is added in a specified amount as inhibitor, lubricant, reservoir protectant and accelerator.

Then, the dynamic contamination of the amphiphobic composite material to the well core is measured with the method specified in the industry standard SY/T5358-2010 for dynamic contamination test, to characterize the change of core permeability and contamination depth before/after drilling fluid contamination.

The results are shown in Table 5.

TABLE 5

| Drilling Fluid | Content of amphiphobic composite material AN-1 wt % | $K_1$/mD | $K_2$/mD | R/% | Contamination depth/cm |
|---|---|---|---|---|---|
| 1# | 0 | 19.74 | 14.22 | 72.03 | 1.25 |
| 2# | 0.1 | 20.68 | 15.49 | 74.90 | 1.05 |
| 2# | 0.2 | 19.45 | 16.13 | 82.93 | 0.88 |
| 2# | 0.3 | 21.23 | 18.77 | 88.41 | 0.70 |
| 2# | 0.4 | 20.47 | 18.15 | 88.67 | 0.70 |
| 2# | 0.5 | 21.28 | 19.02 | 89.37 | 0.69 |

Note:
$K_1$ - Initial permeability of well core;
$K_2$ - Permeability of well core after contamination;
R - Recovery ratio of core permeability It is seen from the results in Table 5: the amphiphobic composite material provided in the present invention can effectively improve the recovery ratio of permeability of dynamically contaminated well core and decreases the well core contamination depth as well, and it is an excellent reservoir protectant. Compared with the original drilling fluid system, as the concentration of the amphiphobic composite material is increased, the recovery ratio of permeability of the well core is increased continuously. When the concentration of the amphiphobic composite material is 0.3 wt %, the recovery ratio of permeability of the well core is as high as 88%, and the contamination depth is decreased to 0.70 cm. That indicates the amphiphobic composite material provided in the present invention also has excellent reservoir protection performance.

Test Case 6

Composition of water-based drilling fluid 1#: 4 wt % sodium bentonite (from Weifang Huawei Bentonite Technology Research Center, the same below), 0.5 wt % sulfomethylated phenolic resin filtrate reducer (SMP-II from Xinxiang Xinlei Oil Field Additives Co., Ltd., the same below), 1 wt % albino asphalt plugging agent (from Henan Haiyang Chemical Co., Ltd.), and 1 wt % starch; in addition, water and barite are added to adjust the density of the drilling fluid to 1.2 g/cm$^3$.

Composition of water-based drilling fluid 2#: the composition of the water-based drilling fluid 1# is used, but the difference is that 0.3 wt % amphiphobic composite material AN-1 is added as inhibitor, lubricant, reservoir protectant and accelerator.

The rheological property and filtrate loss property of such a water-based drilling fluid before aging and after aging at 120° C. for 16 h are tested. The result are shown in Table 6, wherein:

AV refers to apparent viscosity, and is measured with a Fann six-speed viscosity meter, in unit of mPa·s, $$AV = \frac{1}{2}\theta_{600};$$

PV refers to plastic viscosity, and is measured with a Fann six-speed viscosity meter, in unit of mPa·s, PV=$\theta_{600}$−$\theta_{300}$;
YP refers to yield point, and is obtained through calculation from the data measured with a Fann six-speed viscosity meter, in unit of Pa, YP=0.511($\theta_{300}$−PV);
Ratio of yield point to plastic viscosity=YP/PV;
$G_{10''}/G_{10'}$ refers to initial gel strength/final gel strength, and is obtained through calculation from the data measured with a Fann six-speed viscosity meter, in unit of Pa,
Initial Gel Strength=0.511$\theta_3$(10 s)
Final Gel Strength=0.511$\theta_3$(10 min.);
API refers to medium pressure filtrate loss, and is measured with an API filter tester, in unit of mL;
HTHP refers to high-temperature and high-pressure filtrate loss, and is measured with an HTHP filter tester, in unit of mL.

TABLE 6

| Drilling Fluid | AV mPa·s | PV mPa·s | YP Pa | YP/PV Pa/mP·s | $G_{10''}/G_{10'}$ Pa/Pa | API mL | HTHP mL |
|---|---|---|---|---|---|---|---|
| Before aging | | | | | | | |
| 1# | 57.5 | 46 | 11.5 | 0.25 | 2/13 | 6.6 | / |
| 2# | 57.5 | 43 | 14.5 | 0.34 | 2.5/14 | 3.8 | / |
| After aging for 16 h at 120° C. | | | | | | | |
| 1# | 67.5 | 51 | 16.5 | 0.32 | 5/19.5 | / | 14.0 |
| 2# | 61 | 45 | 16 | 0.36 | 3.5/15.5 | / | 10.2 |

It is seen from the data in Table 6: through comparison between the drilling fluid system 1# in which no amphiphobic composite material in the present invention is added and the drilling fluid system 2# in which 0.3 wt % amphiphobic composite material is added, it is found that the amphiphobic composite material has no obvious influence on the rheological property of the entire system at 25° C. normal temperature.

It is found after aging at 120° C.: the apparent viscosity of the drilling fluid system 2# is decreased to a certain degree when compared with the apparent viscosity of the drilling fluid system 1#; under a condition of the same density, the lower viscosity of the system after high temperature aging is helpful for reducing circulation loss and increasing penetration rate; in addition, after aging at 120° C., the API filtrate loss and HTHP filtrate loss of the drilling fluid system 2# are decreased to a certain degree when compared with those of the drilling fluid system 1#. That indicates the amphiphobic composite material provided in the present invention has high compatibility when it is used as amphiphobic inhibitor, lubricant, reservoir protectant and accelerator in the water-based drilling fluid system, and is suitable for use in the water-based drilling fluid.

Test Case 7

Preparation of base mud: 40 g sodium bentonite (from Weifang Huawei Bentonite Technology Research Center) and 3 g anhydrous sodium carbonate are added into 1 L water, the mixture is stirred at a high stirring rate for 5 h, and kept in still state in a sealed state at room temperature for 24 h for curing, to obtain fresh water base mud that has 4 wt % soil content.

The above-mentioned base mud and the base muds in which the amphiphobic composite material AN-1 is added in specified contents (the contents are shown in Table 7) are tested for the influence on the penetration rate of drilling fluid; next, the base muds are aged at 150° C. for 16 h, and then are measured again for the change of penetration rate; the results are shown in Table 7.

Wherein, measurement of penetration rate of drilling fluid: an acceleration tester is used to measure the change of average penetration rate in the test fluids before/after aging at 150° C. for 16 h.

TABLE 7

| | Average penetration rate/ cm * min$^{-1}$ | Increase ratio of average penetration rate |
|---|---|---|
| | Before aging | |
| Base mud | 0.95 | / |
| Base mud + 0.1 wt % AN-1 | 1.12 | 17.89% |
| Base mud + 0.2 wt % AN-1 | 1.27 | 33.68% |
| Base mud + 0.3 wt % AN-1 | 1.41 | 48.52% |
| Base mud + 0.4 wt % AN-1 | 1.43 | 50.52% |
| Base mud + 0.5 wt % AN-1 | 1.41 | 48.42% |
| | After aging for 16 h at 150° C. | |
| Base mud | 1.15 | / |
| Base mud + 0.1 wt % AN-1 | 1.29 | 12.17% |
| Base mud + 0.2 wt % AN-1 | 1.48 | 28.70% |
| Base mud + 0.3 wt % AN-1 | 1.62 | 40.87% |
| Base mud + 0.4 wt % AN-1 | 1.67 | 45.22% |
| Base mud + 0.5 wt % AN-1 | 1.69 | 46.96% |

It is seen from the results in Table 7: the super-amphiphobic composite material provided in the present invention can effectively improve the average penetration rate of the base mud of drilling fluid and attain a purpose of increasing penetration rate, has excellent acceleration performance, and is an outstanding super-amphiphobic accelerator.

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

The invention claimed is:

1. A method for preparing an amphiphobic composite material, comprising:
    performing a first mixing of a nano-titanium dioxide and a nano-silicon dioxide in an alcohol-water mixed solvent under alkaline conditions, to obtain a dispersion of nano-titanium dioxide and nano-silicon dioxide;
    introducing a fluorosilicone-containing coupler into the dispersion of nano-titanium dioxide and nano-silicon dioxide and performing a second mixing; and performing a solid-liquid separation of the product of the second mixing to obtain the amphiphobic composite material;
    wherein, a molar ratio of the titanium dioxide to the silicon dioxide to the fluorosilicone-containing coupler is 1:0.5-5:0.01-0.5, a particle size of the nano-titanium dioxide is 50-500 nm, and a particle size of the nano-silicon dioxide is 50-500 nm.

2. The method according to claim 1, wherein the molar ratio of the titanium dioxide to the silicon dioxide to the fluorosilicone-containing coupler is 1: 1-3:0.05-0.2.

3. The method according to claim 1, wherein the particle size of the nano-titanium dioxide is 50-200 nm, and the particle size of the nano-silicon dioxide is 50-200 nm.

4. The method according to claim 1, wherein the fluorosilicone-containing coupler is one or more of heptadecafluorodecyl trimethoxysilane, heptadecafluorodecyl triethoxysilane, tridecafluorooctyl trimethoxysilane, tridecafluorooctyl triethoxysilane, dodecafluoroheptyl trimethoxysilane, dodecafluoroheptyl triethoxysilane, nonafluorohexyl trimethoxysilane, nonafluorohexyl triethoxysilane, pentafluorophenyl trimethoxysilane, and pentafluorophenyl triethoxysilane.

5. The method according to claim 1, wherein the step of performing a first mixing is performed at a pH of 8-10.

6. The method according to claim 5, wherein the step of performing a first mixing is performed at a pH of 8-9.

7. The method according to claim 1, where in the step of performing a first mixing, there is 500-1,500 mL of the alcohol-water mixed solvent per 100 g of the total weight of the nano-titanium dioxide and the nano-silicon dioxide.

8. The method according to claim 7, wherein the alcohol-water mixed solvent has volume ratio of alcohol solvent to water of 1:2-10.

9. The method according to claim 7, wherein the alcohol-water mixed solvent includes an alcohol solvent, and the alcohol solvent is one or more of ethanol, methanol, n-propanol, and iso-propanol.

10. The method according to claim 1, wherein the step of performing a first mixing includes mixing by ultrasonic dispersion, and conditions in the step of performing a first mixing include: a temperature of 10-40° C., an ultrasonic dispersion time of 10-30 min; and
    wherein the step of performing a second mixing includes mixing by stirring, and conditions in the step of performing a second mixing include: a temperature of 55-95° C., a stirring rate of 200-500 rpm, a time of 8-20 h.

11. The method according to claim 2, wherein the particle size of the nano-titanium dioxide is 50-200 nm, and the particle size of the nano-silicon dioxide is 50-200 nm.

12. The method according to claim 11, wherein the fluorosilicone-containing coupler is one or more of heptadecafluorodecyl trimethoxysilane, heptadecafluorodecyl triethoxysilane, tridecafluorooctyl trimethoxysilane, tridecafluorooctyl triethoxysilane, dodecafluoroheptyl trimethoxysilane, dodecafluoroheptyl triethoxysilane, nonafluorohexyl trimethoxysilane, nonafluorohexyl triethoxysilane, pentafluorophenyl trimethoxysilane, and pentafluorophenyl triethoxysilane.

13. An amphiphobic composite material prepared by the method of claim 1.

14. The amphiphobic composite material according to claim 13, wherein the molar ratio of the titanium dioxide to the silicon dioxide to the fluorosilicone-containing coupler is 1: 1-3:0.05-0.2.

15. A water-based drilling fluid containing the amphiphobic composite material according to claim 13.

16. The water-based drilling fluid according to claim 15, wherein the water-based drilling fluid includes a content of the amphiphobic composite material of 0.1-0.5 wt % based on total weight of the water-based drilling fluid excluding a weighting agent.

17. The water-based drilling fluid according to claim 16, wherein the water-based drilling fluid includes a content of the amphiphobic composite material of 0.2-0.5 wt % based on total weight of the water-based drilling fluid excluding a weighting agent.

18. A method of drilling an oil or gas well comprising;
    drilling a well, and
    adding the water-based drilling fluid of claim 16 to the well.

* * * * *